United States Patent [19]

Schaefer et al.

[11] Patent Number: 5,410,584
[45] Date of Patent: Apr. 25, 1995

[54] APPARATUS FOR SUPPORTING A RADIATION TRANSMITTER

[75] Inventors: Willi Schaefer, Erlangen; Klaus Thormann, Forchheim; Olaf Bransky, Neunkirchen, all of Germany

[73] Assignee: Siemens Aktiengesellschaft, Munich, Germany

[21] Appl. No.: 224,408

[22] Filed: Apr. 7, 1994

Related U.S. Application Data

[63] Continuation of Ser. No. 36,237, Mar. 24, 1993, abandoned.

[30] Foreign Application Priority Data

Apr. 29, 1992 [DE] Germany .......................... 42 14 087.0

[51] Int. Cl.⁶ ............................................... H05G 1/02
[52] U.S. Cl. ..................................................... 378/196
[58] Field of Search ................ 378/196, 193, 195, 197, 378/198, 208

[56] References Cited

U.S. PATENT DOCUMENTS 3,670,163  6/1972  Lajus .
5,050,204  9/1991  Siczek et al. .......................... 378/197

FOREIGN PATENT DOCUMENTS 1466880  2/1969  Germany .
4111780  10/1992  Germany .
1352444  5/1974  United Kingdom .

*Primary Examiner*—David P. Porta
*Attorney, Agent, or Firm*—Hill, Steadman & Simpson

[57] ABSTRACT

An apparatus for supporting a radiation transmitter has a first C-arm carrying the radiation transmitter at one end thereof, which is mounted so as to be movable within a holder, the holder in turn being mounted so as to be movable along a second C-arm. The second C-arm is adjustably mounted within an installation room.

16 Claims, 2 Drawing Sheets

APPARATUS FOR SUPPORTING A RADIATION TRANSMITTER

This is a continuation of application Ser. No. 08/036,237, filed Mar. 24, 1993.

BACKGROUND OF THE INVENTION

1. Field of the Invention

The present invention is directed to an apparatus for supporting a radiation transmitter, of the type wherein the radiation transmitter is mounted at one end of a C-arm.

2. Description of the Prior Art

It is well-known to attach a radiation transmitter, such as an x-ray radiator in an x-ray diagnostics apparatus, at one end of a C-arm, with a radiation receiver disposed at the opposite end of the C-arm. Such an arrangement is described, for example in German OS 14 66 880. The C-arm is mounted in the installation room so as to be height-adjustable along its circumference by means of a vertical column, as well as being pivotable around a horizontal axis. The vertical column is mounted so as to be displaceable in a plane along ceiling rails. The spatial adjustment of the unit formed by the x-ray radiator and the radiation receiver is accomplished by appropriate motor drives, which can be operated by a control device.

Since the C-arm is displaceable along its circumference within its holder, oblique projections of an examination subject can be made by swiveling the unit formed by the x-ray radiator and the image receiver on the C-arm, thereby producing exposures of an examination subject from different directions. If the C-arm is in the form of a semi-circle, swiveling through approximately ±90° can be achieved. Although the C-arm could be lengthened, for example, to form three-quarters of a circle, which would increase the swiveling range, such a lengthening of the C-arm degrades the manipulability of the apparatus.

SUMMARY OF THE INVENTION

It is an object of the present invention to provide an apparatus for supporting a radiation transmitter of the type employing a C-arm with the radiation transmitter mounted at one end thereof, wherein the swiveling range of the radiation transmitter is optimally large, without having a disadvantageous influence on the manipulability of the apparatus.

The above object is achieved in accordance with the principles of the present invention in an apparatus for supporting a radiation transmitter wherein the radiation transmitter is mounted at the end of a first C-arm, which is mounted in a holder, and the holder is mounted so as to be movable along a second C-arm.

The structure of this apparatus achieves the advantage that the radiation transmitter is not only movable in a manner corresponding to the circumference of the first C-arm, but us additionally movable corresponding to the circumference of the second C-arm. This results in an apparatus which is easy to manipulate, and which occupies a space which relatively small.

Preferably a radiation receiver is disposed at the opposite end of the first C-arm, so that the apparatus can be employed in an x-ray diagnostics installation.

If the imaging scale is to be variable, the radiation receiver is preferably adjustable along a central axis of the radiation transmitter.

The spatial adjustability of the radiation transmitter and/or the radiation receiver is enhanced in an embodiment wherein the second C-arm is adjustable around a vertical axis as well as being height-adjustable, either by means of a ceiling rail arrangement or a floor rail arrangement, or a combination of both.

If the second C-arm has a free end, i.e., if only a floor rail arrangement or only a ceiling rail arrangement is employed, a locking mechanism can be provided at the free end for stabilizing the apparatus in an exposure position, after being moved to that position.

Preferably a control device is provided for facilitating operation of the apparatus by spatially displacing one or both of the C-arms, as well as all other mechanisms which are employed for spatially displacing the supported components of the radiation transmitter and / or the radiation receiver.

DESCRIPTION OF THE PREFERRED EMBODIMENTS

Figure 1:
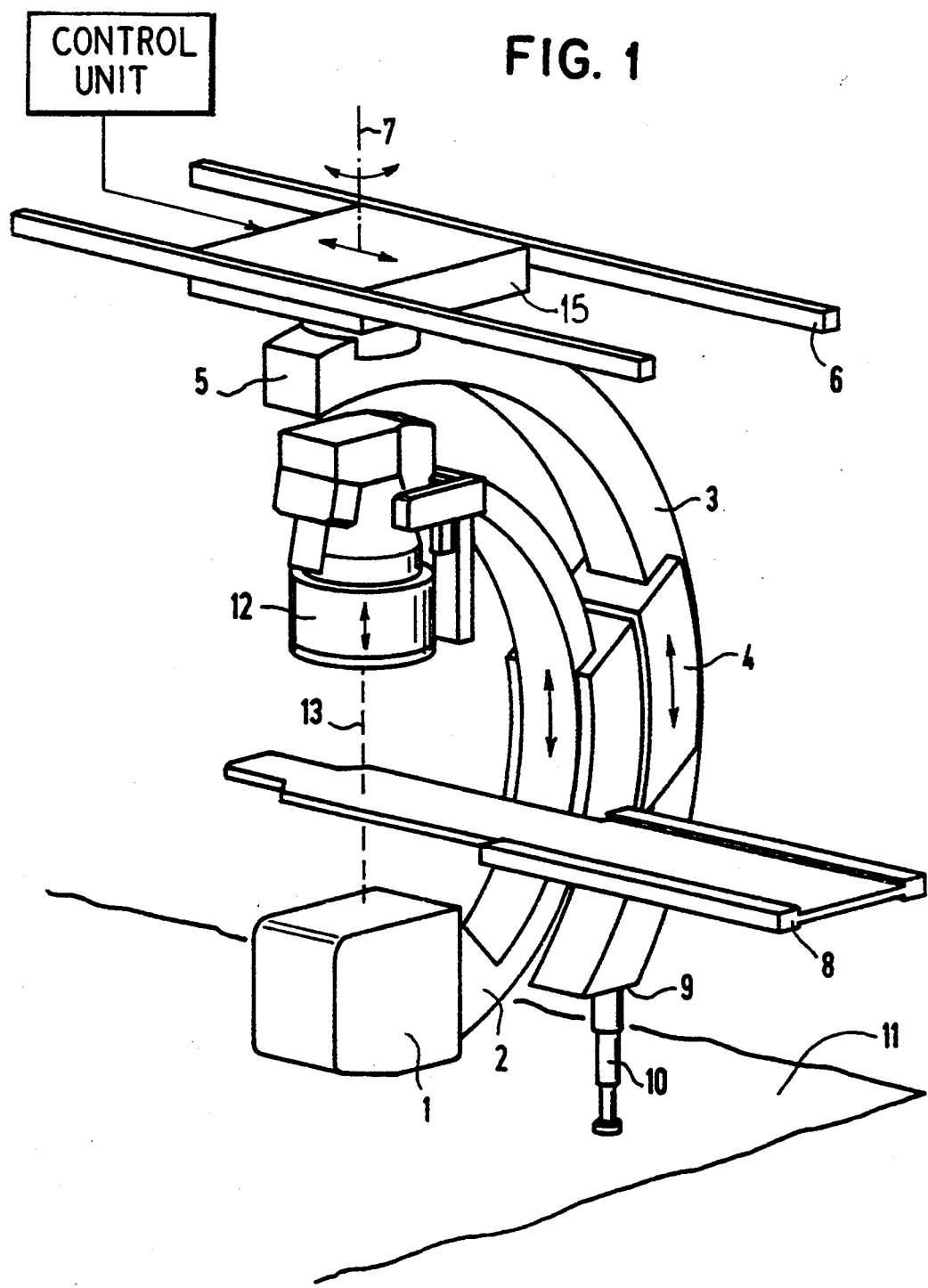
FIG. 1 is a perspective view of an apparatus constructed in accordance with the principles of the present invention for supporting a radiation transmitter, in an embodiment mounted on ceiling rails.

As shown in FIG. 1, an apparatus for supporting a radiation transmitter 1 includes a first C-arm 2 with the radiation transmitter 1 mounted at one end thereof. The radiation transmitter 1 may be of any type, and it is of no consequence to the invention whether the radiation transmitter 1 emits ionizing radiation or electromagnetic radiation or acoustic waves.

The first C-arm 2 is carried by a second C-arm 3 by means of a mount or holder 4, so that the C-arm 2 is a movable along its circumference within the holder 4, as indicated by the double arrow in the drawing on the C-arm 2. The range of movement of the radiation transmitter 1 is enlarged if the mount 4 is also adjustable along the circumference of the second C-arm 3, as indicated by the double arrow in the drawing on the holder 4. The holder 4 is moveable along the circumference of the second C-arm 3 so that the holder 4 is pivotable through at least 90°. When the holder 4 is moveable the radiation transmitter 1 can be moved not only through the circumference of the first C-arm 2, but also through the circumference of the second C-arm 3. The range of movement is thus enlarged, while preserving a compact structure and a good manipulability of the apparatus.

Preferably one end 5 of the C-arm 3 is held by a suitable mount 15 for displacing the C-arm 3 in a plane along a ceiling rail arrangement 6, as indicated by the double arrow on the mount 15. The mount 15 also permits the second C-arm 3 to be pivoted around a vertical axis 7, as indicated by the double arrow curved around the vertical axis 7. Both C-arms 2 and 3 can thus be moved around the vertical axis 7, so that the apparatus, for treatment or examination of a subject, can be displaced to a location at which it does not impede access to the subject. It will be understood that the apparatus could be mounted at its lower end by means of a floor rail arrangement similar to the ceiling rail arrangement 6, or by a combination of floor and ceiling rails.

The mount 15 is preferably adjustable in steps, automatically or under the control of an operator, by means of a control unit 14, so that the C-arms 2 and 3 and the radiation transmitter 1 are moved step-by-step along the longitudinal axis of a patient support 8. The patient support 8 is shown for clarity as simply extending into the opening of the C-arm 2, however, it will be understood that suitable supporting elements, which are not shown in the drawing, will be provided for the support table 8. During the step-by-step adjustment of the position of the radiation transmitter 1, the holder 4 is adjusted via the control unit 14 so that insofar as possible, the center of mass of the overall apparatus substantially coincides with the center of gravity, or is optimally close thereto. Vibrations of the apparatus which may otherwise occur during the step-by-step adjustment are thus reduced.

If a subject on a patient support 8 is to be examined or treated, the free end 9 of the second C-arm 3 can be locked in a specific position on the floor 11 by means of a locking mechanism 10. The locking mechanism 10 may be, for example, a hydraulic telescoping leg, with one end attached to the free end 9 of the second C-arm 3 and the other end coming to rest on the floor 11. The actuation of the locking mechanism 10 can ensue on the basis of suitable control from the control unit 14 as soon as the overall apparatus reaches the specified position.

Figure 2:
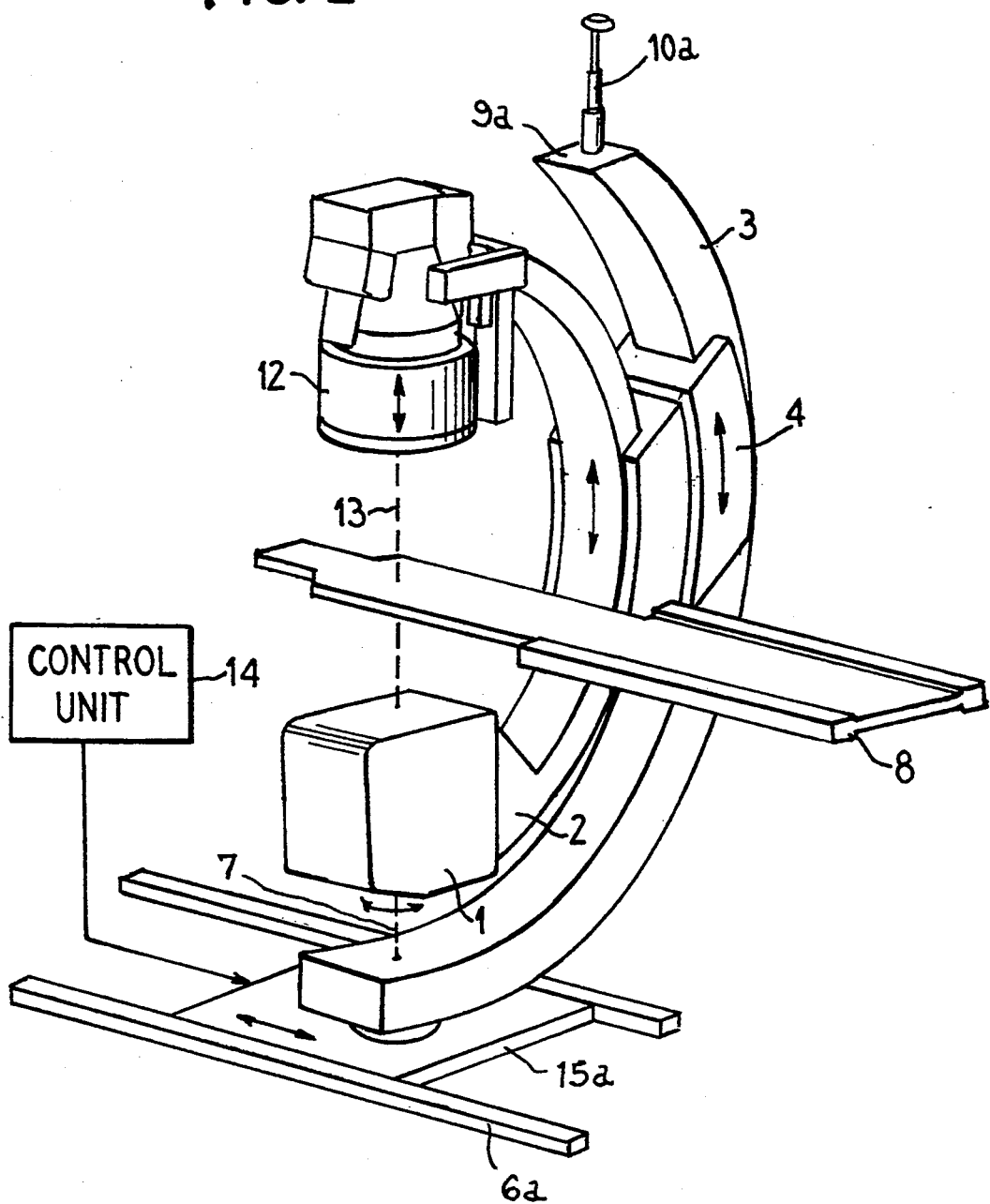
FIG. 2 is a perspective view of an apparatus constructed in accordance with the principles of the present invention for supporting irradiation transmitter, in an embodiment mounted on floor rails.

In the embodiment of FIG. 2, the second C-arm 3 is mounted on floor rails 6a on which a mount 15a can slide, the second C-arm 3 being rotatable around the vertical axis 7 on the mount 15a. A locking mechanism 10a is mounted at an upper free end 9a of the second C-arm 3, so as to support the second C-arm 3 against the ceiling of the installation space. Movement of the individual components in the embodiment of FIG. 2 takes place in the same manner as described in connection with the embodiment of FIG. 1, under the control of the control unit 14.

If the radiation transmitter 1 is an x-ray radiator, a radiation receiver in the form of an x-ray image intensifier 12 may be disposed at the opposite end of the first C-arm 2. The apparatus is then suitable for use in an x-ray diagnostics installation. It is preferable that the x-ray image intensifier 12 be adjustable along the central ray 13 of the x-ray radiator, as indicated by the vertical double arrow in the drawing on the x-ray image intensifier 12. This enables the magnification scale of an image of an examination area, produced from the signals of the image intensifier 12, to be varied. Oblique projections can be obtained by moving the C-arm 2 and/or the holder 4 in the directions of the double arrows respectively indicated thereon, which cause a rotation of the entire unit formed by the x-ray radiator and the image intensifier 12 through angles greater than ±90°, due to the fashioning of the apparatus of the invention.

In order to avoid damage to the x-ray radiator and/or to the x-ray image intensifier during movement thereof, known anti-collision sensors can be provided at the exposed faces of one or components, which will immediately stop further adjustment of the apparatus when actuated.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for supporting a radiation transmitter comprising:
    a radiation transmitter;
    a first C-arm with said radiation transmitter mounted at one end thereof;
    a second C-arm having a vertical axis extending therethrough;
    means for mounting said second C-arm in an installation space permitting rotation of said second C-arm around said vertical axis; and
    holder means for holding said first C-arm and for permitting movement of said first C-arm within said holder means along the circumference of said first C-arm and for mounting said first C-arm on said second C-arm and permitting movement of said holder along the circumference of said second C-arm.

2. An apparatus as claimed in claim 1 further comprising a radiation receiver disposed at an opposite end of said first C-arm.

3. An apparatus as claimed in claim 2 wherein said radiation transmitter has a central axis, and further comprising means for adjusting said radiation receiver along said central axis.

4. An apparatus as claimed in claim 1 further comprising means for mounting said second C-arm in said installation space including a ceiling rail arrangement and means for rotating said second C-arm around a vertical axis.

5. An apparatus as claimed in claim 1 further comprising means for mounting said second C-arm in said installation space including a floor rail arrangement and means for rotating said second C-arm around a vertical axis.

6. An apparatus as claimed in claim 1 wherein said second C-arm has a free end and further comprising means disposed at said free end of said second C-arm for locking said second C-arm at a selected position in said installation space.

7. An apparatus as claimed in claim 1 further comprising control means for spatially adjusting said first and second C-arms.

8. An apparatus for supporting a radiation transmitter in an installation space, comprising:
    a radiation transmitter;
    a first C-arm with said radiation transmitter mounted at one end thereof, said first C-arm having a circumference;
    a second C-arm, said second C-arm having a circumference;
    means for stationarily mounting said second C-arm in said installation space which prevents movement of said second C-arm along said circumference of said second C-arm for maintaining said second C-arm in a fixed circumferential relation to said installation space; and
    holder means for holding said first C-arm and for permitting movement of said first C-arm within said holder means along the circumference of said first C-arm and for mounting said first C-arm on said second C-arm and permitting movement of said holder means along the circumference of said second C-arm, said second C-arm having a length permitting movement of said holder means along said circumference of said second C-arm to pivot said holder means through at least 90°.

9. An apparatus as claimed in claim 8 further comprising a radiation receiver disposed at an opposite end of said first C-arm.

10. An apparatus as claimed in claim 9 wherein said radiation transmitter has a central axis, and further comprising means for adjusting said radiation receiver along said central axis.

11. An apparatus as claimed in claim 8 wherein said means for stationarily mounting said second C-arm in said installation space comprises a ceiling rail arrangement and means for rotating said second C-arm around a vertical axis.

12. An apparatus as claimed in claim 8 wherein said means for stationarily mounting said second C-arm in said installation space comprises a floor rail arrangement and means for rotating said second C-arm around a vertical axis.

13. An apparatus as claimed in claim 8 wherein said second C-arm has a free end and further comprising means disposed at said free end of said second C-arm for locking said second C-arm at a selected position in said installation space.

14. An apparatus as claimed in claim 8 further comprising control means for spatially adjusting said first and second C-arms.

15. An apparatus as claimed in claim 8 wherein said second C-arm has a vertical axis extending therethrough, and wherein said means for stationarily mounting said second C-arm in said installation space comprises means for permitting displacement of said second C-arm in said installation space exclusively in a single direction relative to said vertical axis.

16. An apparatus as claimed in claim 15 wherein said means for stationarily mounting said second C-arm in said installation space comprises means for permitting displacement of said second C-arm exclusively in a single direction perpendicular to said vertical axis.

* * * * *